United States Patent [19]

Kreyenhagen et al.

[11] Patent Number: 5,154,183
[45] Date of Patent: Oct. 13, 1992

[54] BIPOLAR MYOCARDIAL ELECTRODE ASSEMBLY

[75] Inventors: Paul E. Kreyenhagen, Castaic; John R. Helland, Saugus, both of Calif.

[73] Assignee: Siemens-Pacesetter, Inc., Sylmar, Calif.

[21] Appl. No.: 590,898

[22] Filed: Oct. 1, 1990

[51] Int. Cl.⁵ .............................................. A61N 1/05
[52] U.S. Cl. .................................... 128/785; 128/642
[58] Field of Search ................. 128/642, 784, 785, 786

[56] References Cited

U.S. PATENT DOCUMENTS

| | | | |
|---|---|---|---|
| 4,010,758 | 3/1977 | Rockland et al. | 128/418 |
| 4,256,115 | 3/1981 | Bilitch | 128/785 |
| 4,355,642 | 10/1982 | Alferness | 128/785 |
| 4,357,946 | 11/1982 | Dutcher et al. | 128/785 |

Primary Examiner—William E. Kamm
Assistant Examiner—Scott M. Getzow
Attorney, Agent, or Firm—Leslie S. Miller; Malcolm J. Romano

[57] ABSTRACT

A bipolar electrode assembly for attachment to heart tissue for use with a pacemaker. The assembly has a hub member with a helical screw-in coil that acts as a first electrode and is used to attach the assembly to the heart tissue. The assembly further comprises a plurality of appendages that extend from the hub member and each have an electrode segment of electrically conductive material. The electrode segment of the appendages can act together as a single second electrode, or alternatively as a separate, independent electrodes, which may selectively be used for pacing or sensing. The electrode segments not only act as electrodes, but also allows heart tissue to grow directly into the conductive material to help secure the assembly to the heart. The assembly also has apertures and grooves for suture connection of the assembly to the heart. Methods of manufacturing the assembly and connecting the assembly to a heart are also described.

41 Claims, 2 Drawing Sheets

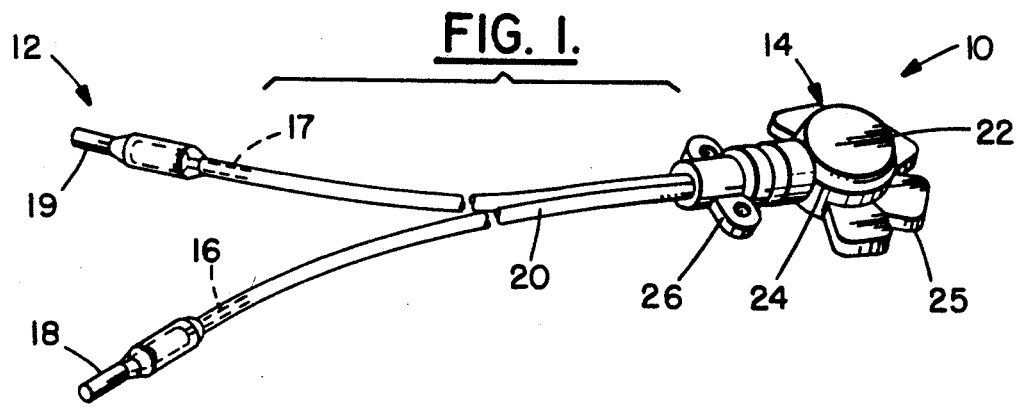
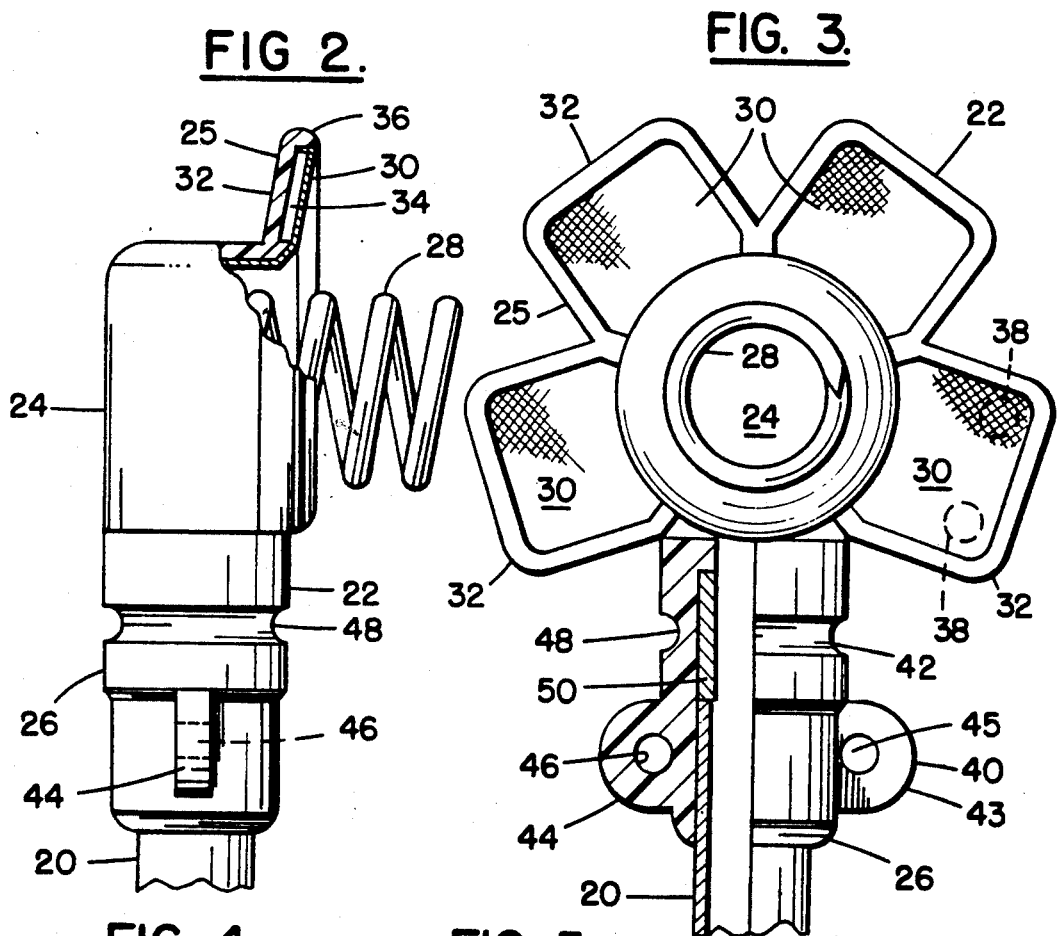
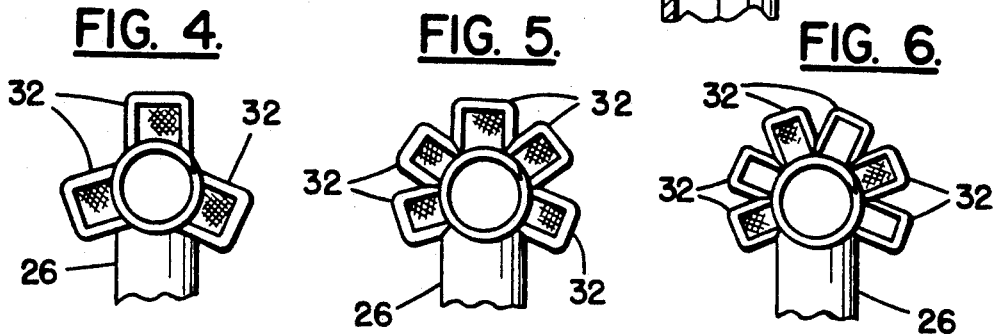

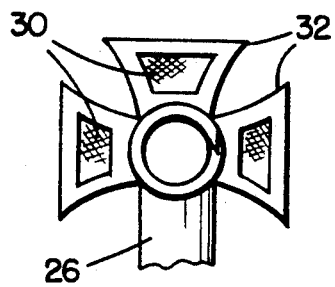
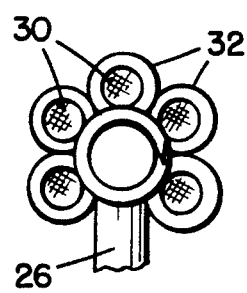
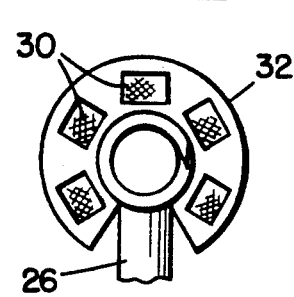
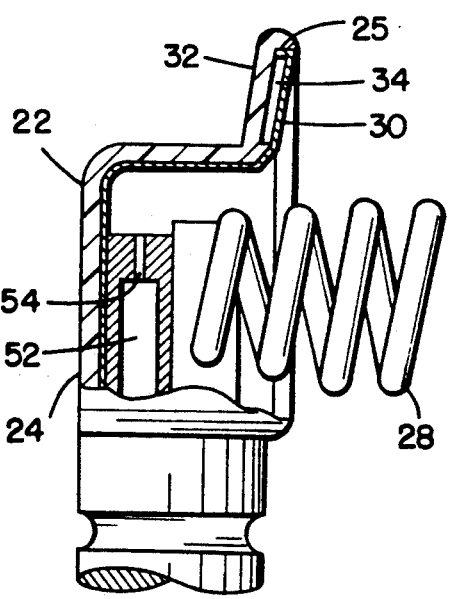
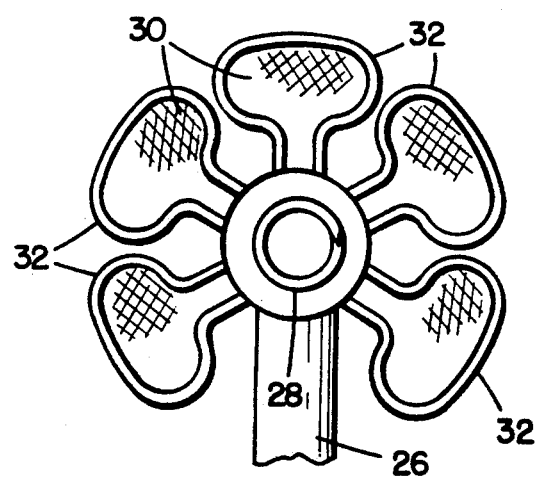

BIPOLAR MYOCARDIAL ELECTRODE ASSEMBLY

BACKGROUND OF THE INVENTION

Field of the Invention

The present invention relates generally to cardiac electrode assemblies, and more particularly to a bipolar myocardial electrode assembly adapted to be electrically and mechanically connected to heart tissue.

Electrical simulation of body tissue and organs as a method of treating various pathological conditions and providing appropriate therapies is quite common-place. Such electrical simulation necessarily requires some manner of making electrical contact with the body tissue or organ. One example of such therapy is the use of a pacemaker to provide electrical pulses through electrical wires, called leads, to cause the diseased heart of a patient to beat normally. Pacemaker leads have electrodes located on the distal end of the lead for contacting the tissue of the heart. In the case of a patient who is having surgery only to install a pacemaker and one or more leads, transvenous leads which enter the heart through a vein are typically utilized. Transvenous leads contact the heart tissue inside the heart, and do not require opening the chest of the patient in a procedure known as a thoracotomy for the leads to be installed.

However, in the case of a patient who is having open heart surgery and who will require cardiac pacing following the surgery, electrical leads may be placed on the outside of the heart on the epicardial surface or into the myocardial tissues during a thoracotomy, during which procedure the heart tissue is exposed. Such electrodes are typically referred to as myocardial or epicardial leads. Examples of procedures in which the patient's heart will be exposed by a thoracotomy include a cardiac artery bypass procedure, corrective cardiac surgery for congenital defects, heart valve replacement, and the installation of an automatic implantable cardiac defibrillator (AICD). If following the procedure the patient will require cardiac pacing, it is expedient to install pacing electrodes while the patient's heart is exposed.

There are additional situations in which the installation of transvenous pacing leads will not be possible. These situations include the case when the vein which would be used is damaged or too small, or the situation in which a physical or anatomical anomaly prevents the placement of a transvenous lead within the heart, or in the case where an artificial heart valve is present. In these cases, the use of a myocardial lead is necessary.

A number of different myocardial electrode structures have been developed, as have various techniques for implanting those electrode structures into the myocardial tissue of the heart. Typically, myocardial electrodes are attached to the exterior of the heart, so that they may be stimulated by a cardiac pacemaker which is also implanted within the patient's body. The electrodes of myocardial leads are installed by being brought into electrical contact with the heart, and then sutured and/or secured in place with some fixation means.

It is generally preferable to use a plurality of myocardial electrodes rather than a single electrode (and the pacemaker can as the other electrode) to prevent inadvertent stimulation of skeletal muscle or other tissue from occurring during cardiac pacing. Thus, at least two electrodes are needed to provide effective stimulation and sensing of the heart. Use of two electrodes both mounted on the heart is known as bipolar pacing. It is undesirable to use two distinct myocardial leads each containing a single electrode in that the number of leads as well as the surgical steps required to implant a plurality of electrodes are increased. As the number of leads is increased, the size of the surgical opening into the patient's body, the number of wounds into the heart and the resultant trauma of the entire surgical procedure are increased. Thus, rather than installing two separate unipolar myocardial leads, it is preferable to install a single bipolar or multipolar myocardial lead.

One such bipolar myocardial lead is disclosed in U.S. Pat. No. 4,010,758, to Rockland et al. The Rockland et al. lead utilizes a bipolar body tissue electrode having a first electrode in a helical (screw-in) configuration, and an annularly configured second electrode surrounding the helical first electrode. A sheet of netting is used in the Rockland et al. device to enhance fibrotic growth.

A significant problem associated with cardiac electrode assemblies is that prior myocardial lead designs have not used electrodes designed to provide edge effects (increased electrical field density at an electrode caused by a conductive surface meeting a conductive edge of the electrode) efficiently. An increase in edge effects can increase the intensity and focus of electrical fields and provide for appropriate cardiac muscle stimulation with significantly less energy consumption. It is an objective of the present invention to use edge effects to greater advantage than is done in the art.

A related problem associated with cardiac pacemakers relates to the fact that pacemakers use an internal power source (typically a battery) with a limited life. After an extended period of time, such as five years, the implanted pacemaker must be removed (because its power source is depleted) and replaced with a new pacemaker. Therefore, it is an objective to minimize the electrical current drain on the power source by appropriate design of the pacemaker's electrodes to provide for reduced stimulation voltage, while still maintaining the strength of the resultant electric field through the myocardium at a sufficiently high level to stimulate the heart.

A further problem associated with cardiac electrode assemblies is that prior art myocardial lead assemblies are relatively rigid and do not conform to the shape of the myocardial surface and its motion during cardiac contractions and rest periods. Thus, the area of contact between myocardial lead electrode(s) and its (their) edges, and the heart tissue was not either complete or intimately mobile. It is an objective of the present invention to provide a myocardial lead which ensures reliable and intimate, non-traumatic contact with the heart tissue, and which will maintain that contact during both heart contractions and rest periods.

A still further problem associated with previously known myocardial electrode assemblies is that they do not provide suitable means, other than a single screw-in helix (or a single barb), for securing the assembly to the heart tissue. Although a screw-in helix electrode is a fairly good means to attach an electrode assembly to heart tissue, under certain circumstances it is desirable to provide additional securing means to prevent disattachment of the lead's electrode assembly from the heart. Accordingly, it is an objective of the present invention to provide improved means for securing the electrode portion of the lead to the heart.

An additional problem associated with cardiac electrodes assemblies in the prior art is that they did not have additional pacing electrodes or integral sensor electrodes, but rather required additional separate electrodes to be connected to the heart tissue. The connection of separate additional electrodes to the heart tissue increases trauma to the heart and increases the risk of a failure with an increased number of connections to the heart. Accordingly, it is an objective of the present invention to optionally provide such additional electrodes for stimulation and sensing in a single myocardial lead.

Finally, it is also an objective that all of the aforesaid advantages and objectives be achieved without incurring any substantial relative disadvantage.

SUMMARY OF THE INVENTION

The disadvantages and limitations of the background art discussed above are overcome and other advantages are provided by the improved bipolar myocardial electrode assembly of present invention.

In accordance with one embodiment of the present invention, a bipolar electrode assembly is provided for attachment to heart tissue of a living animal. The assembly comprises of a center section and a plurality of leaf-shaped appendages (or "petals") extending outwardly therefrom. The center section has a first member comprised of electrically conductive material and has a distal end with means for connecting to the heart tissue. The leaf-shaped appendages are fixedly connected to the center section and extend radially outwardly from the center section.

Each leaf-shaped appendage includes at least one electrode segment. The electrode segments may be any one of a variety of electrically conductive configurations, including, but not limited to, a metallic mesh, a wire coil, a braided wire segment, metallic spots, points, or dots, a flat conductive surface, a microporous metallic surface, or a conductive polymer. The leaf-shaped appendages and/or the center section also include means for electrically insulating the conductive elements on the leaf-shaped appendages from the first member.

In accordance with another embodiment of the present invention a bipolar heart electrode assembly is provided comprising a first electrode, a second electrode and means for housing and at least partially electrically insulating the first and second electrodes. The first electrode has a distal end with a screw-in helix. The second electrode has a distal portion with a plurality of leaf-shaped appendages extending radially outwardly from the screw-in helix and in a substantially perpendicular fashion. The housing means includes apparatus for connecting a suture to fixedly secure the housing means directly to heart tissue.

In accordance with one method of the invention, a method of manufacturing a bipolar heart electrode is provided comprising the steps of providing a first electrode having a screw-in helix at a distal end, and a second electrode having a plurality of electrically conductive leaf-shaped appendages at a distal end; mechanically connecting the second electrode with the first electrode, the two electrodes remaining electrically isolated but having a fixed orientation at their distal ends with the leaf-shaped appendages of the second electrode extending radially outwardly from the first electrode distal end; and providing an electrically insulating housing around portions of the first and second electrodes.

In accordance with another method of the present invention, a method of connecting a bipolar heart electrode assembly to a heart is provided comprising the steps of providing an electrode assembly having a distal end with a first electrode having a screw-in helix, a second electrode having conductive members extending generally radially outwardly from a center axis of the helix, and a housing at least partially insulating the first and second electrodes; screwing the screw-in helix into the heart, the radially outwardly extending conductive members advancing with the screw-in helix and contacting the surface of the heart; and fixedly connecting the housing to the heart by means of a suture at least until such time as heart tissue can grow into the radially outwardly extending conductive members of the second electrode.

In accordance with another embodiment of the present invention, a bipolar heart electrode assembly is provided comprising a housing, a first electrode, and a second electrode. The first electrode is at least partially contained in the housing and has a distal end screw-in helix. The second electrode has a distal end with a substantially flat, "T" shape which is fixedly mechanically, but not electrically, connected by the base of the "T" to the first electrode distal end and orientated in a manner extending radially outwardly from the screw-in helix. The second electrode distal end is suitably shaped to have a substantially large outer perimeter, but relatively small area to thereby increase edge effects in the relatively small area.

In another alternate embodiment, the myocardial lead of the present invention is made with the helical screw-in first electrode, with a plurality of independent, non-electrically connected second electrodes radiating radially outwardly from the first electrode. The first electrode and any one of the second electrodes may be utilized to provide either an electrical pulse to the heart, or sensed cardiac signals.

In still another alternate embodiment, the bipolar myocardial lead is made with a medication dispensing or eluting capability. Such medications may include steroids to reduce threshold over a period of time following implant, or other pharmacologic agents which could affect cardiac rhythm or contractility.

It may therefore be seen that the present invention teaches a myocardial electrode which uses edge effects to significantly greater advantage than is done in the art. The improved myocardial lead of the present invention thereby minimizes the electrical current drain on the power source by appropriate design of the pacemaker's electrodes, while maintaining the strength of the resultant electric field through the myocardium at a sufficiently high level to stimulate the heart. The present invention also provides a myocardial lead which conforms to the heart's surface and flexes to ensure reliable contact with the heart tissue, and which will maintain that contact during both heart contractions and rest periods.

In addition, the myocardial lead of the present invention provides improved means for securing the electrode portion of the lead to the heart. It allows for the provision of additional electrodes for performing both stimulation and sensing in a single myocardial lead. Finally, all of the aforesaid advantages and objectives are achieved without incurring any substantial relative disadvantage.

DESCRIPTION OF THE DRAWINGS

The foregoing aspects and other features of the invention are explained in the following description, taken in connection with the accompanying drawings, wherein:

FIG. 1 is a perspective view of a bipolar myocardial electrode assembly incorporating features of the present invention;

FIG. 2 is an enlarged plan side view of the distal end of the electrode assembly shown in FIG. 1 with a partial cutaway section;

FIG. 3 is a plan front view of the assembly distal end as shown in FIG. 2 with a partial cutaway section;

FIG. 4 is a partial schematic front view of the distal end of a first alternate embodiment of the present invention;

FIG. 5 is a partial schematic front view of the distal end of a second alternate embodiment of the present invention;

FIG. 6 is a partial schematic front view of the distal end of a third alternate embodiment of the present invention;

FIG. 7 is a partial schematic front view of the distal end of a fourth alternate embodiment of the present invention;

FIG. 8 is a partial schematic front view of the distal end of a fifth alternate embodiment of the present invention;

FIG. 9 is a partial schematic front view of the distal end of a sixth alternate embodiment of the present invention;

FIG. 10 is a partial schematic front view of the distal end of a seventh alternate embodiment of the present invention; and FIG. 11 is a schematic side view of the distal end of an alternate embodiment of the present invention with a partial cutaway view, with the alternate embodiment shown being a steroid eluting embodiment.

DETAILED DESCRIPTION OF THE PREFERRED EMBODIMENT

Referring to FIGS. 1 through 3, there is shown a bipolar myocardial electrode assembly 10 incorporating features of the present invention. The assembly 10 generally comprises a proximal end 12 and a distal end or head 14. Two conductors or leads 16 and 17 extend between the proximal end 12 and distal end 14 and are each terminated at the proximal end by connectors 18 and 19. Those skilled in the art will immediately appreciate that a single bipolar or multipolar lead body and/or connector (not shown) could also be utilized.

A suitable insulative casing 20 is provided for each of the conductors made from a suitable insulative material such as silicone rubber. However, any suitable type of insulative medical-grade material (which is biocompatible and biostable) may be used. The length of the leads 16 and 17 will be similar to conventional myocardial leads.

Referring specifically to FIGS. 2 and 3, the distal end of head 14 of the assembly 10 generally comprises a center or hub section 24, an outer periphery section 25, and an anchoring section 26. In the preferred embodiment, the head 14 has a housing 22 (which may be in any of the configurations shown herein, or in other, similar configurations) which is comprised of a suitable insulating material such as silicone rubber. It will be appreciated, however, that any suitable type of insulative medical-grade material may be used.

Fixedly mounted together with the housing 22 is a first member 28 and a plurality of second members 30. The first member 28 is comprised of a relatively rigid biocompatible and biostable electrically conductive material such as platinum-iridium, and, in the preferred embodiment, is shaped in the form of a screw-in helix. Other configurations of the first member 28 could also be utilized without departing from the principles of the present invention; for example, a barbed hook, a staple, or other tissue fixation means could also be used. The first member 28 is electrically connected to the first conductor 18, and forms a first electrode which may be screwed into the heart tissue of a patient.

A plurality of second members 30 extend radially outwardly from the hub section 24, and are in a plane approximately perpendicular to the axis of the first member 28. (In the preferred embodiment, the second members will be flexed forward to embrace the tissue of the heart, and will flex forward and backward to move with the tissue of the heart.) In the embodiment shown, there are four second members covered by the housing 22.

The second members 30, in the embodiment shown, are made of a relatively flexible biocompatible and biostable electrically conductive material such as platinum, platinum iridium, titanium, Elgiloy, or a metal substrate coated with iridium oxide, titanium nitride, platinum, or carbon. However, any suitable material can be used with any suitable type of coating.

The second members may be in any of a wide variety of mechanical configurations, including, but not limited to, a metallic mesh, one or more wire coils, a braided wire segment, metallic spots or dimples, points, or dots, a flat conductive surface, a microporous metallic surface, or a conductive polymer. The second members may also be made of a material which is a combination of an electrically conductive material and a nonconductive material. The form shown in the accompanying figures is that of a wire mesh. The wire mesh, in the embodiments shown, is made of wire cloth, but may alternatively be comprised of an expanded mesh or perforated holes in a solid member. Portions of the mesh could also be comprised of a nonconductive material such as Dacron. Alternatively, any of the other mechanical forms of materials could instead be used.

In the embodiment shown, the second members 30 are all electrically connected to the second conductor 17 and together form a second electrode. The head 14 has an outer periphery section 25, in the embodiment shown, with the second members comprising four leaf-shaped appendages or leaves 32. Each leaf-shaped appendage 32 is comprised of a portion of the housing 22 and forms a section of the collective second member 30. In the preferred embodiment, the four sections of the collective second member 30 may be formed of a single segment of material.

The leaf-shaped appendage portions of the collective second member 30 are connected to the leaf-shaped appendage portions of the housing 22 and each forms a space 34 therebetween. However, the space 34 need not be provided. An edge or bead 36 (which is part of the housing 22) is located at the outer edges of the leaf-shaped appendage portions of the second members 30 such that sharp edges of the second members 30 do not irritate the heart tissue.

The leaf-shaped appendages 32 extend radially outwardly relative to the center axis of the screw-in helix 28 in a substantially perpendicular fashion, but are angled slightly forward, as shown in FIG. 2, to form a generally frustroconical shape. The leaf-shaped appendages 32, in the embodiment shown, are preferably slightly flexible such that when the head 14 is screwed into a patient's heart by the first electrode 28, the leaf-shaped appendages 32 can contact the surface of the heart and flex back slightly to provide constant and conformal intimate contact with the heart and flex with movement of the heart tissue.

The leaf-shaped appendages 32 can also be provided with apertures 38 such that sutures (not shown) may be passed therethrough to fixedly connect the leaf-shaped appendages 32 to the heart tissue. Although the second electrodes 30 have been described above as a single member with multiple leaf-shaped appendage portions, it should be understood that the second electrode or conductor material can be comprised of multiple segments of conductive material.

In addition, not all of the second electrodes 30 need be electrically connected to each other. Individual electrodes 30 may be electrically isolated from each other such that one or more of the electrodes 30 may be used as a second electrode, but one or more of the other electrodes 30 may also be used as a third electrode for such purposes as sensing. By separating the sensing feature from the pacing electrodes, a much more sensitive means is provided to more effectively detect signals and/or transmit stimuli.

Although only two conductors are shown in this embodiment, such an alternate embodiment would include three or more conductors. In fact, if desired, each of the electrodes 30 may have a separate conductor (not shown) terminating in one or more connectors. Thus, the pacemaker (not shown) could individually address each of the second electrodes, and selectively use any or all of them for pacing and/or for sensing.

In the prior art the pacing electrodes were also used for sensing, but the electrodes tend to become polarized which can easily mask the evoked response signal of the myocardium. Thus, in the prior art, the evoked response could not be easily detected if capture occurred. Nor could the shape of the ventricular and/or atrial depolarizations be properly detected.

With the assembly having separate pacing and sensing electrode pads as described above, intrinsic activity immediately after the pacing pulse can be detected. This information may be used by the pulse generator to alter its output (i.e. to lower the output voltage or current of the pacemaker if it can be verified that capture occurred), or to alter the pacing rate. This represents a tremendous advantage over the previously known myocardial pacing leads. Thus, this can prolong the working life of the pacemaker battery, and/or be utilized to provide a rate response capability or other therapeutic capability. In short, if the shape of the intrinsic depolarization can be detected, it may be evaluated; pacemaker functions, such as output, rate, and delay times, can thereby be modulated.

The anchoring section 26, in the embodiment shown, generally comprises an eyelet section 40 and a suture groove section 42. The eyelet section 40 comprises two laterally extending sections 43 and 44 with suture apertures 45 and 46, which may be used to fixedly connect the anchoring section 26 of the housing to the heart tissue. However, the eyelet section 40 is optional, and need not be provided.

The suture groove section 42 comprises an annular groove 48 around the anchoring section 26, and a compression protection member 50 located under the housing 22 at the groove 48. Thus, the groove 48 may be used to fixedly connect the anchoring section 26 to the heart tissue via a suture (not shown) without risk of the head 14 moving relative to the suture. The compression protection member 50 prevents the conductors or insulation of leads 16 and 17 from being damaged when the suture is tightly tied.

In the preferred embodiment the protection member is made of hard plastic. However, any mechanically suitable material may be used.

The conductors 16 and 17 are connected to the first and second members 28 and 30 within the hub section 24 or the anchoring section 26. Thus, by providing additional means for connecting the anchoring section 26 to the heart tissue, there is a decreased risk that the conductors 16 and 17 may have a damaged or faulty connection at the assembly head 14.

Another principal feature of the present invention is the novel use of a conductive porous material as the second electrode. In addition to functioning as an electrode, the conductive porous material and configuration also provide the additional function of promoting more rapid fibrosis into the electrode material, into the spaces 34, and around the leaf-shaped appendages 32. This thereby provides a more secure and permanent placement of the assembly without having to provide a separate electrode and a separate net as disclosed in the Rockland et al. described above. The present invention provides both functions with one element thereby reducing both manufacturing costs and clinical complexity.

In order to manufacture the assembly 10, the first electrode 28 is mechanically, but not electrically, connected with the second electrode 30. (Optionally, the second electrodes 30 may also be electrically isolated and connected to different leads.) This can occur either before or after the connection of the conductors 16 and 17 to the electrodes 28 and 30. The first and second electrodes remain electrically isolated, but have a substantially fixed orientation at their distal ends with the leaf-shaped appendage portions of the second electrodes 30 extending radially outwardly and substantially perpendicularly away from the center axis of the first electrode 28. The housing 22 can be utilized to electrically insulate a majority of the first and second electrodes except for those portions of the electrodes intended to make electrical contact with the heart tissue.

In order to connect the assembly 10 to the heart, the screw-in helix 28 is screwed into the heart tissue with the conductive sections of the leaf-shaped appendages advancing with the screw-in helix and contacting the surface of the heart. The assembly can be left with merely the screw-in helix 28 fixedly connecting the assembly 10 to the heart tissue until the heart tissue grows into the mesh of the second electrode 30. Alternately, sutures may be placed at one or more of the groove 48, the eyelet sections 43 and 44, and the leaf-shaped appendage apertures 38.

The embodiment shown in FIGS. 1 through 3 has four leaf-shaped appendages. From two to ten leaf-shaped appendages may be utilized, although three to six represent the preferred embodiment. Referring also to FIGS. 4 through 10, alternate embodiments of the invention having different numbers and configurations of the leaf-shaped members are shown. As can be seen, any suitable number of leaf-shaped appendages can be provided.

FIG. 4 shows an assembly with three leaf-shaped appendages. FIG. 5 shows an assembly with five leaf-shaped appendages. FIG. 6 shows an assembly with six leaf-shaped appendages. Although the shape of the leaf-shaped appendages and the area of contact of the conductive material 30 with the heart tissue for each of the embodiments shown in FIG. 1-6 is generally square, any suitable shape may be provided. FIG. 7 shows an assembly with three triangular leaf-shaped appendages. FIG. 8 shows an assembly with five circular leaf-shaped appendages. FIG. 10 shows an assembly with five "T" configuration leaf-shaped appendages.

FIG. 9 shows a single arc-shaped appendage with five areas of conductive material 30. In this embodiment, the material used for the housing 22 would preferably be more highly flexible than is necessary in the other embodiments.

One of the principal features of the present invention is that, due to the use of leaf-shaped appendages as an electrode, the total length of the perimeter of the edges of the second electrodes 30 is significantly increased when compared to a mere disk electrode as in the prior art (Rockland et al.) with the same amount of surface area. This increased perimeter or edge length allows for more efficient use of edge effects.

Edge effects, as described above, is the increased electrical field intensity located at the edge of an electrode. and is caused by a conductive surface meeting an edge (either an edge of the conductor a point at which the conductor is covered by an insulative edge). By increasing the edge length of the second electrodes 30, the present invention increases the intensity of electrical fields in the area of the head 14 such that efficient cardiac pacing can be provided with significantly reduced energy usage. (In addition, of course, the significant advantage of enhanced sensing capability is also achieved.)

Thus, the pacemaker battery life is prolonged due to a reduced level of energy usage. FIG. 10 shows the most edge effect-enhanced embodiment in the figures, with the leaf-shaped appendages having nonuniform edges or nonsymmetrical shapes to maximize edge effects. These nonsymetrical shapes may also enhance sensing capabilities. Additionally, each second electrode surface 30 may also be designed to have edge effects. (For example, the second electrode surfaces 30 may have grooves therein.) Some of the leaf-shaped appendages may be designed specifically for enhanced pacing, while others may be designed specifically for enhanced sensing.

Other alternative shaped leaf-shaped appendages might include triangles, squares, rectangles, curved leaf-shaped appendages, hexagons, octagons, butterfly shapes or others, or combinations of different shapes as well as combinations of straight and curved edges.

Referring next to FIG. 11, there is shown a further alternate embodiment of the present invention. In the embodiment shown, the head 14 also comprises a reservoir 52 which can contain a suitable drug or chemical, such as a steroid or antiarrhythmic substance in a liquid form. (It will also be appreciated by those skilled in the art that the space 34 could be used to store a drug or chemical.) In the embodiment shown, the assembly also comprises a liquid flow restrictor 54 at the mouth of the reservoir 52, such that the chemical may be released slowly.

Obviously, the amount of flow and size of the reservoir may be selected such that upon reaching the expected chronic pacing thresholds levels and/or the expected chronic cardiac signal sensing levels over a predictable period of time, the chemical becomes depleted. Another embodiment of the present invention could also provide that the silicone rubber head 14, (or the leaf-shaped appendages) is impregnated with or provided with a supply of a drug or chemical. The chemical could then be dispensed or elute over a period of time.

One such chemical would be a steroid in the form of sodium salt of dexamethansone phosphate, a glucocorticosteriod. As the steroid is eluted, development of fibrous tissue around the assembly can be suppressed, thereby decreasing acute pacing thresholds and improving cardiac signal sensing. In another alternate embodiment the assembly could have multiple reservoirs of chemicals.

It may therefore be appreciated from the above detailed description of the preferred embodiment of the present invention that it teaches a myocardial electrode which uses edge effects to significantly greater advantage than is done in the art. The improved myocardial lead of the present invention thereby minimizes the electrical current drain on the power source by appropriate design of the pacemaker's electrodes, while maintaining the strength of the resultant electric field through the myocardium at a sufficiently high level to stimulate the heart. The present invention also provides a myocardial lead which flexes to ensure reliable and conformal intimate contact with the heart tissue, and which will maintain that contact during both heart contractions and rest periods.

In addition, the myocardial lead of the present invention provides improved means for securing the electrode portion of the lead to the heart. It allows for the provision of additional electrodes for performing both stimulation and sensing in a single myocardial lead. Finally, all of the aforesaid advantages and objectives are achieved without incurring any substantial relative disadvantage.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A multipolar electrode assembly for attachment to myocardial heart tissue of a living animal, said multipolar electrode assembly comprising:

a conductive, helically-shaped electrode member having a proximal end and a distal end, said distal end of said helically-shaped electrode member being adapted for connecting to heart tissue;

a hub member made of nonelectrically conductive material, said proximal end of said helically-shaped electrode member being received in said hub member; and a plurality of appendages fixedly mechanically connected to and extending radially outwardly from said hub member, each of said appendages comprising:
- a segment of electrically conductive material which is not electrically connected to said helically-shaped electrode member, said segment of electrically conductive material having a surface adapted for contacting heart tissue; and
- means for electrically insulating a side of said segment of conductive material opposite said surface adapted for contacting heart tissue, said insulating means being connected to said hub member.

2. A multipolar electrode assembly as defined in claim wherein said helically-shaped electrode member is relatively rigid and is adapted to be rotatably inserted into heart tissue.

3. A multipolar electrode assembly as defined in claim wherein said helically-shaped electrode member is made of platinum-iridium.

4. A multipolar electrode assembly as defined in claim 1, wherein said hub member and said insulating means are made of medical-grade silicone rubber.

5. A multipolar electrode assembly as defined in claim 1, wherein said hub member is essentially circular in cross-sectional configuration, said plurality of appendages being mechanically connected to said hub member at the perimeter of said hub member.

6. A multipolar electrode assembly as defined in claim 1, wherein said plurality of appendages are connected to said hub member at a slight angle relative to a plane orthogonal to a longitudinal axis of said helically-shaped electrode member to form a frustroconical shape, the interior of said frustroconical shape facing said distal end of said helically-shaped electrode member.

7. A multipolar electrode assembly as defined in claim 6, wherein said plurality of appendages are adapted to be at least partially angularly flexible with respect to said longitudinal axis of said helically-shaped electrode member to allow said plurality of appendages to conform to the surface of the heart.

8. A multipolar electrode assembly as defined in claim 7, wherein said segments of electrically conductive material are at least partially flexible.

9. A multipolar electrode assembly as defined in claim wherein there are between two and ten appendages connected to said hub member, said appendages being adjacent one another.

10. A multipolar electrode assembly as defined in claim 9, wherein there are between three and six of said appendages.

11. A multipolar electrode assembly as defined in claim 1, wherein said segments of conductive material are made of a material from the group consisting of platinum, platinum iridium, titanium, Elgiloy, and a metal substrate coated with iridium oxide, titanium nitride, platinum, or carbon.

12. A multipolar electrode assembly as defined in claim 1, wherein said segments of conductive material are made of a material from the group consisting of a metallic mesh, one or more wire coils, a braided wire segment, metallic spots or dimples, points, or dots, a flat conductive surface, a microporous metallic surface, and a conductive polymer.

13. A multipolar electrode assembly as defined in claim 1, wherein said segments of electrically conductive material are comprised of both electrically conductive metallic material and nonconductive material.

14. A multipolar electrode assembly as defined in claim 1, wherein said insulating means and said segments of electrically conductive material cooperate to form spaces therebetween.

15. A multipolar electrode assembly as defined in claim 14, wherein said electrically conductive material is porous to allow heart tissue to grow therethrough into said spaces.

16. A multipolar electrode assembly as defined in claim 14, wherein said spaces comprise:
- means for dispensing a therapeutic medication or chemical over a period of time.

17. A multipolar electrode assembly as defined in claim 1, wherein said appendages comprise:
- apertures located therein for receiving sutures to secure said appendage ends to the heart tissue.

18. A multipolar electrode assembly as defined in claim 1, additionally comprising:
- means for anchoring said multipolar electrode assembly.

19. A multipolar electrode assembly as defined in claim 18, wherein said anchoring means comprises:
- an anchoring member located adjacent a side of said hub member, said anchoring member having a circumferential groove located therein; and
- two laterally extending segments mounted on opposite sides of said anchoring member, said laterally extending segments having suture apertures therein.

20. A multipolar electrode assembly as defined in claim 1, wherein said hub member comprises:
- means for storing a therapeutic medication or chemical which may be dispensed over a period of time.

21. A multipolar electrode assembly as defined in claim 20, wherein said storing means comprises:
- at least one chemical reservoir with a flow restricting device which can slowly release said therapeutic medication or chemical to treat the heart tissue.

22. A multipolar electrode assembly as defined in claim 20, wherein said therapeutic medication or chemical is compounded into a solid material which is stored in said hub member.

23. A multipolar electrode assembly as defined in claim 1, wherein said segments of electrically conductive material are arranged and configured to enhance their edge effect characteristics.

24. A multipolar electrode assembly as defined in claim 23, wherein said segments of electrically conductive material have irregular configurations to increase their perimeter to area ratio.

25. A multipolar electrode assembly as defined in claim 1, wherein at least two of said segments of electrically conductive material are electrically connected together.

26. A multipolar electrode assembly as defined in claim 1, wherein at least two of said segments of electrically conductive material are electrically separate from each other.

27. A multipolar electrode assembly as defined in claim 1, wherein at least one of said segments of electrically conductive material is an electrode member for delivering, together with said helically-shaped electrode member, a stimulus to the heart tissue.

28. A multipolar electrode assembly as defined in claim 27, wherein at least one of said segments of electrically conductive material is an electrode member for sensing, together with said helically-shaped electrode member, signals from the heart tissue.

29. A multipolar electrode assembly as defined in claim 28, additionally comprising:
- a first insulated conductor having a distal end and a proximal end, said distal end of said first insulated conductor being electrically connected to said helically-shaped electrode member;
- a second insulated conductor having a distal end and a proximal end, said distal end of said second insulated conductor being electrically connected to at least one of said at least one of said segments of electrically conductive material which is an electrode member for delivering a stimulus; and
- a third insulated conductor having a distal end and a proximal end, said distal end of said third insulated conductor being electrically connected to at least one of said at least one of said segments of electrically conductive material which is an electrode member for sensing signals from the heart tissue.

30. A multipolar electrode assembly as defined in claim 27, additionally comprising:
- a first insulated conductor having a distal end and a proximal end, said distal end of said first insulated conductor being electrically connected to said helically-shaped electrode member; and
- a second insulated conductor having a distal end and a proximal end, said distal end of said second insulated conductor being electrically connected to at least one of said at least one of said segments of electrically conductive material which is an electrode member for delivering a stimulus.

31. A multipolar heart electrode assembly comprising:
- a first electrode having a distal end with a screw-in helix;
- a second electrode having a distal end with a plurality of appendages extending radially outwardly away from said screw-in helix in substantially perpendicular fashion; and
- means for housing and at least partially electrically insulating said first and second electrodes, said means for housing including means for connecting a suture to said means for housing to fixedly secure said means for housing directly to heart tissue.

32. A multipolar heart electrode assembly as defined in claim 31, wherein said means for connecting includes eyelet apertures.

33. A multipolar heart electrode assembly as defined in claim 31, wherein said means for connecting includes a suture groove.

34. A multipolar heart electrode assembly as defined in claim 33, wherein said means for housing includes a lead protector located under said suture groove comprised of a hard material to prevent damage to leads due to compression of said means for housing by a suture at said suture groove.

35. A multipolar heart electrode assembly as defined in claim 31, wherein said means for connecting includes suture apertures at ends of said appendages for connecting said ends to heart tissue by sutures passing through said apertures.

36. A multipolar heart electrode assembly, comprising:
- a first electrode having a distal end with a screw-in helix;
- a second electrode having a distal end with at least one appendage extending radially outwardly away from said screw-in helix in substantially perpendicular fashion; and
- means for housing and at least partially electrically insulating said first and second electrodes.

37. A multipolar electrode assembly for attachment to myocardial heart tissue of a living animal, said multipolar electrode assembly comprising:
- a conductive electrode member having a proximal end and a distal end, said distal end of said electrode member comprising fixation means adapted for insertion into heart tissue;
- a hub member made of nonelectrically conductive material, said proximal end of said electrode member being received in said hub member; and
- a plurality of appendages fixedly mechanically connected to and extending radially outwardly from said hub member, each of said appendages comprising:
  - a segment of electrically conductive material which is not electrically connected to said helically-shaped electrode member, said segment of electrically conductive material having a surface adapted for contacting heart tissue; and
  - means for electrically insulating a side of said segment of conductive material opposite said surface adapted for contacting heart tissue, said insulating means being connected to said hub member.

38. A multipolar electrode assembly as defined in claim 37, wherein said fixation means comprises: a barbed member adapted to be inserted into heart tissue.

39. A multipolar electrode assembly as defined in claim 37, wherein said fixation means comprises: a staple member adapted to be inserted into heart tissue.

40. A method of making a multipolar electrode assembly for attachment to myocardial heart tissue of a living animal, said method comprising:
- adapting the distal end of a conductive, helically-shaped electrode member to be connected to heart tissue;
- receiving the proximal end of said helically-shaped electrode member in a hub member made of nonelectrically conductive material; and
- mechanically a plurality of appendages to said hub member in a manner whereby said plurality of appendages extend radially outwardly from said hub member, each of said appendages comprising:
  - a segment of electrically conductive material which is not electrically connected to said helically-shaped electrode member, said segment of electrically conductive material having a surface adapted for contacting heart tissue; and
  - means for electrically insulating a side of said segment of conductive material opposite said surface adapted for contacting heart tissue, said insulating means being connected to said hub member.

41. A method of making a multipolar heart electrode, comprising:
- providing a first electrode having a screw-in helix at a distal end, and a second electrode having a plurality of electrically conductive segments each having a proximal side;
- mechanically mounting said second electrode in spaced arrangement with said first electrode, the two electrodes remaining electrically isolated but having a substantially fixed relative orientation with said second electrodes extending substantially radially outwardly from a proximal end of said first electrode; and
- providing an electrically insulating housing around the proximal end of said first electrode and the proximal sides of said second electrodes.

* * * * *